United States Patent [19]

Ishibashi et al.

[11] Patent Number: 5,414,072
[45] Date of Patent: May 9, 1995

[54] ANTI-OCTOPUS RHODOPSIN MONOCLONAL ANTIBODY

[75] Inventors: Tadashi Ishibashi, Kumagaya; Hiroaki Kezuka, Saitama; Saeko Yoshino, Kawagoe; Norio Shimizu, Sayama; Motoyuki Tsuda, Himeji; Shuji Imazeki, Saitama, all of Japan

[73] Assignee: Hitachi, Ltd., Tokyo, Japan

[21] Appl. No.: 588,783

[22] Filed: Sep. 27, 1990

[30] Foreign Application Pricrity Data

Sep. 27, 1989 [JP] Japan .................................. 1-249138
Feb. 28, 1990 [JP] Japan .................................. 2-45410
May 30, 1990 [JP] Japan .................................. 2-138209

[51] Int. Cl.$^6$ ........................ C07K 15/28; C12N 5/20; C12N 15/02; C12P 21/08
[52] U.S. Cl. ......................... 530/387.9; 530/388.2; 435/240.27; 435/172.2; 435/70.21
[58] Field of Search ................ 530/387, 388.2, 387.9; 435/7.21, 240.27, 172.2

[56] References Cited

U.S. PATENT DOCUMENTS 4,444,878 4/1984 Paulus .

OTHER PUBLICATIONS

Hicks et al. J. Histochem. Cytochem. 35: 1317–1328 1987.
Ovchinnikov et al. FEBS Letters 232: 69–72 1988.
Cambbell, "Monoclonal Antibody Technology" Elsevier Press, 1984.
tokunaga et al. Zoological Science 6: 167–171 1989.
Gert de Covet et al. European J. Cell Biology 38: 106–112 1985.
Adamus et al. Peptide Research 1: 42–47, 1988.
Yamaguchi et al. FEBS Letters 324: 287–292, 1993.
Lehninger, "Biochemistry" 2nd Ed. Worth Publ. Inc. 1975, pp. 106, 560–561.
Nature vol. 244 Jul. 6, 1973 P42–45 Fusion of Two Immunoglobulin-producing Myenoma Cells R. G. H. Cotton & C. Milstein.
J. Membrane Biol. 37 P235–262 (1977) Formation, Structure, and Spectrophotometry of Air–Water Interface films Containing Rodopsin Juan I. Korenbrot & Mary–Jean Pramik.
Abstract of 4th International Conference on Lungmuirl Blodgett Films P490–491 (1989) Formation of Two-Dimensional Protein Domains in Monolayers: Biotinlipids-Strepta Vaidin Interaction R. Blankenburg, P. Meller, H. Ringsdorf & C. Salesse.
2nd International Symposium on Biotronic and Molecular Electronic Devices R & D Association for futrue Electron Devices Dec. 12 0 14 1983 P83–86 Photoreaction of Immobilized Ocupus Rhodopsin Tadasi Ishibashi, Saeko Yoshino, Shuji Imazeki & Norio Shimizu.
Biochimca et Biophysica Acta, 578 (1979) 372–380 Optical Activity of Octopus Metarodoppsins Motoyuki Tsuda.
Proceeding of the Yamada Conference XXI P167–172, 1988 Signal Coupling Proteins in Octopus Photoreceptors Motoyuki Tsuda.
Journal of Neutrocytology 12, 785–803 (1983) The Subcellular Localization of Rat Photoreceptor-Specific Antigens Donna M. Fekete & Colin J. Barnstable.
Biochemistry 1984, 23, 6544–6549 Localization of Binding Sites for Carboxyl Terminal Specific AntiRhodopsin Monoclonal Antibodies Using Synthetic Peptides Donald Mackenzie, Anatol Arendt, Paul Hargrave, J. Hugh McDowell & Robert S. Molday.
J. Cell. Biol. vol. 105 (5 pt.2), 1985, p. 222a, abstract No. 843; L. J. Robles et al.: "Monoclonal antibody localization of opsin in squid photoreceptors".

*Primary Examiner*—Paula K. Hutzell
*Attorney, Agent, or Firm*—Pennie & Edmonds

[57] ABSTRACT

The invention relates to a monoclonal antibody which binds to octopus rhodopsin and octopus metarhodopsin wherein said monoclonal antibody binds with higher affinity to metarhodopsin than to rhodopsin and does not inhibit rhodopsin-metarhodopsin interconversion upon exposure to blue or red light. The monoclonal antibody binds to a peptide having the sequence Val-Ile-Gly-Arg-Pro-Met-Ala-Ala-Ser-Lys-Lys-Met-Ser.
The photochemical reaction of rhodopsin thin layers may be detected using the anti-rhodopsin monoclonal antibodies of the invention.

1 Claim, 5 Drawing Sheets

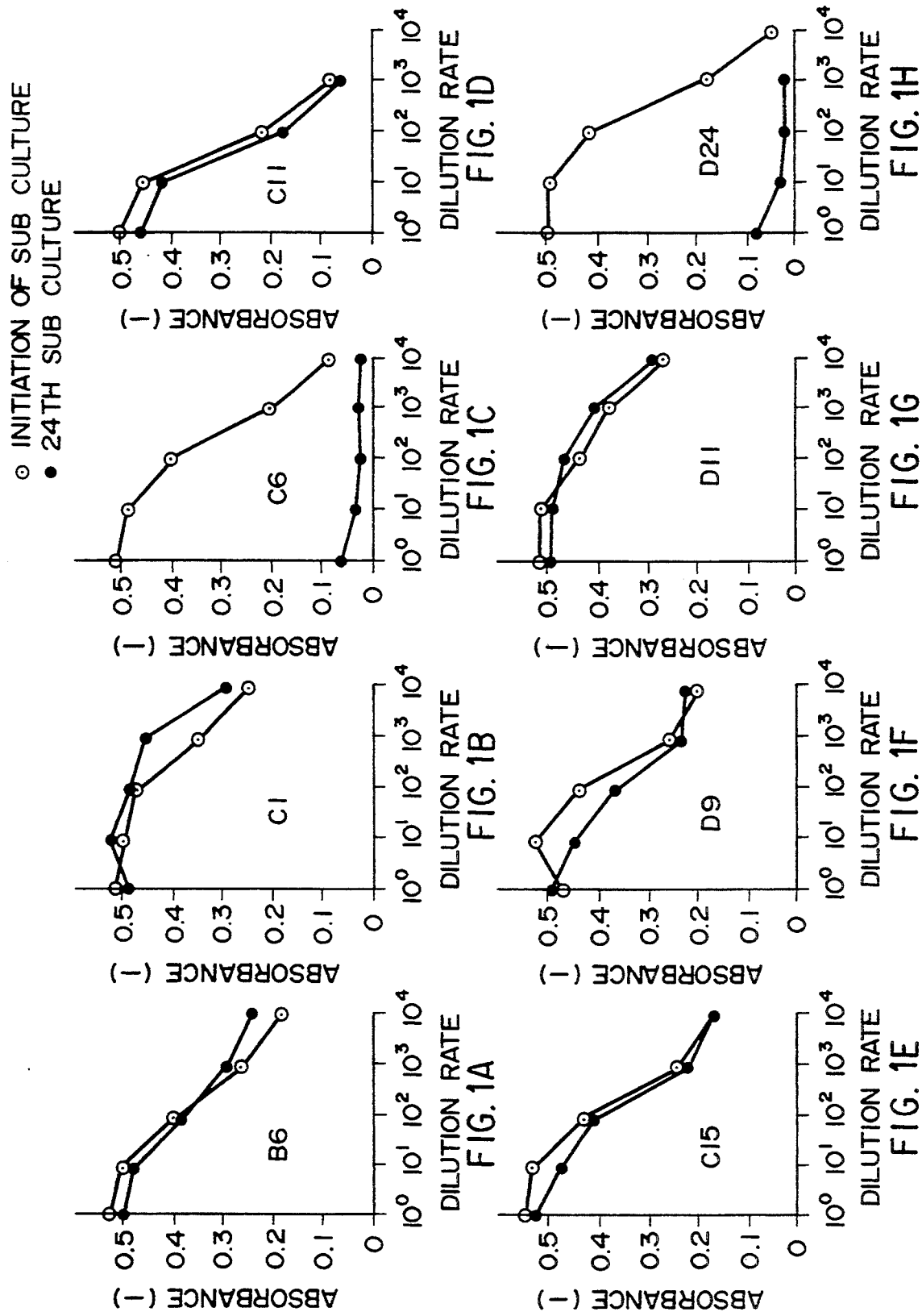

FIG. 2A
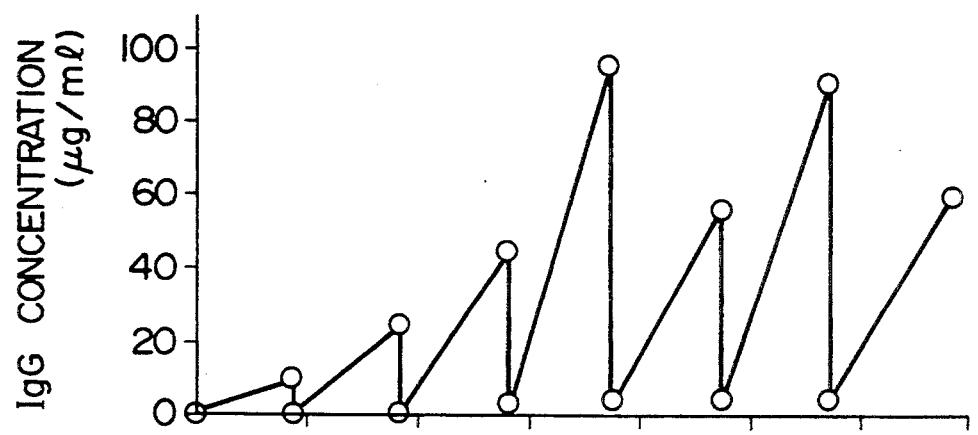
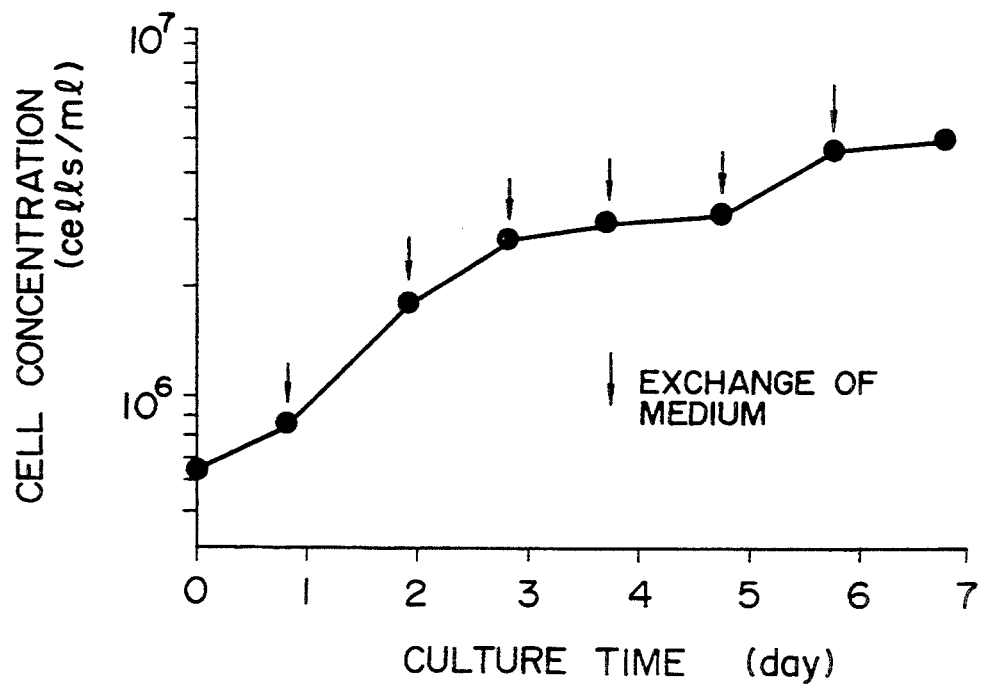
FIG. 2B

F I G. 5A
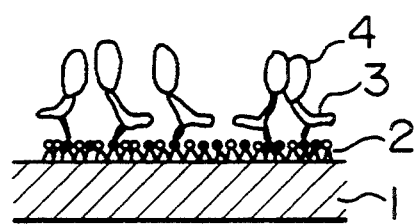
F I G. 5B
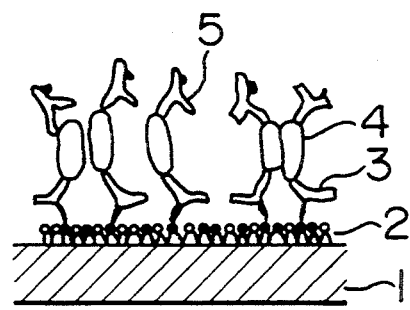
F I G. 6A
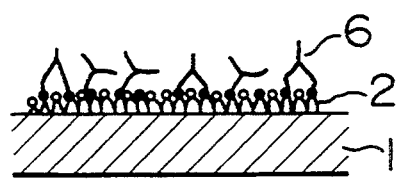

ANTI-OCTOPUS RHODOPSIN MONOCLONAL ANTIBODY

BACKGROUND OF THE INVENTION

1. Field of the Invention

The present invention relates to an anti-rhodopsin monoclonal antibody useful for utilizing rhodopsin as a photosensor, an optical information recognition element, etc. and use thereof.

More particulalry, the present invention relates to an anti-rhodopsin monoclonal antibody which reacts with rhodopsin without inhibiting photochemical reaction of rhodopsin, an anti-rhodopsin monoclonal antibody which has different affinities to rhodopsin and metarhodopsin, a hybrid antibody which can concurrently recognize rhodopsin and a thin layer constituent molecule, a method for fixing or immobilizing rhodopsin using these antibodies, a process for preparing arhodopsin thin layer, a method for photochemical detection of the rhodopsin thin layer, and relates to the rhodopsin thin layer.

2. Related Art Statement

As substances which take part in information processing in vivo, there are known functional proteins such as acetylcholine receptor, rhodopsin, etc. If their functions are artificially exhibited using these functional proteins, it would be possible to provide extremely effective sensors or information processing elements. In order to obtain such sensors or elements, it is necessary to fix these proteins on a carrier or substrate without damaging the functions of proteins.

Rhodopsin is a visual pigment which is a sensor for recognizing optical information and a membrane protein widely distributed in vertebrate and invertebrate species, giving attention to its use as a material for photosensor or optical information recognition element. Rhodopsin consists of opsin protein and 11-cis-retinal. Upon exposure to light, cis-retinal turns to trans-retinal to form metarhodopsin. Color pigments associated with color sense undergoes a similar change. For example, octopus rhodopsin turns, upon exposure to a blue light, to a mixture of photoproducts, metarhodopsin and rhodopsin. In this case, the maximum absorption wavelength is shifted from 475 nm to 500 nm. When exposed to a red light of 580 nm or longer, rhodopsin can be regenerated from metarhodopsin and the maximum adsorption wavelength is reverted to 475 nm [Tsuda, Motoyuki; Biochemica et Biophysica Acta, 578, 372–380 (1979)]. That is, it is considered that in the case of octopus rhodopsin, the two states could be controlled by selecting either a red light or a blue light and octopus rhodopsin would be usable as a photosensor or an optical memory. Color pigments which participates in color sense also undergoes a photochemical reaction similar to-that of rhodopsin. Thus, attention has been focused on rhodopsin-like substances which take part in visual sense.

In order to utilize rhodopsin as a photosensor or an optical memory, it is necessary to immobilize rhodopsin. The Langmuir-Burget method (hereinafter abbreviated as LB method) is known to be a method for fixing protein to prepare a thin layer. It is reported that, for example, bovine rhodopsin is laminated onto a glass plate by the LB method and its photochemical reaction is spectrophotometrically determined [Korenbrat et al., J. Membrane Biol., Vol. 37, 235–263 (1977)]. That is, rhodopsin is incorporated into phosphatidyl choline membrane and spread over the surface of water; the spread layer is transferred to a glass plate to prepare a rhodopsin thin layer.

However, the known technique described above encounters problems that rhodopsin cannot be arranged or fixed in a specific direction, it is difficult to immobilize rhodopsin without damaging the function of rhodopsin, and that rhodopsin cannot be regularly arranged, photochemical reaction of the rhodopsin thin layer cannot be directly detected.

On the other hand, antibodies or monoclonal antibodies have been notably marked out only as probes for tissue distribution or functional analysis of protein but also as materials for fixing functional proteins. For immobilizing rhodopsin using antibodies, there is disclosed in Japanese Patent Application Laid-Open No. 63-111428 a method in which rhodopsin is incorporated into liposome consisting of hapten-bound phospholipid, and the liposome is two-dimensionally arranged on a substrate using an antibody specific to the phospholipid to immobilize rhodopsin thereby to construct a biological element capable of converting external optical information into various ions and chemical substances.

With respect to monoclonal antibodies against rhodopsin, antibodies against bovine, and rat and bacteriorhodopsins are constructed as shown below. C. J. Barnstable et al. constructed monoclonal antibodies capable of recognizing photoreceptor tissue, using the crude membrane component obtained from rat retinas as antigen and, analyzed the structure of the photoreceptor tissue using anti-bovine rhodopsin monoclonal antibodies in combination [J. of Neurocytology, 12, 785–803 (1983)]. D. MacKenzie et al. has also constructed monoclonal antibodies capable of recognizing the C-terminus of bovine rhodopsin and analyzed distribution and change of rhodopsin in visual cell disk membrane [Biochemistry, 23, 6544–6549 (1984)]. However, any anti-rhodopsin monoclonal antibody which is usable as a photosensor or an optical information recognition element, etc. has not been developed so far.

SUMMARY OF THE INVENTION

An object of the present invention is to provide an anti-rhodopsin monoclonal antibody which is useful for utilizing rhodopsin as a photosensor, an optical information recognition element, etc. and to provide hybrid antibody.

Another object of the present invention is to provide a method for immobilizing rhodopsin using an anti-rhodopsin monoclonal antibody or a hybrid antibody.

A further object of the present invention is to provide a process for preparing a rhodopsin thin layer using a hybrid antibody and the thin layer obtained by the process.

A still further object of the present invention is to provide a method for photochemical detection using an anti-rhodopsin monoclonal antibody.

These and other objects of the present invention will be apparent from the following description.

In a first aspect of the present invention, there is provided an anti-rhodopsin monoclonal antibody which is capable of recognizing a stable site of the rhodopsin molecule without inhibiting the photochemical reaction, and a hybridoma capable of producing the monoclonal antibody.

In a second aspect of the present invention, there is provided a method for immobilizing rhodopsin on a carrier using the anti-rhodopsin monoclonal antibody.

In a third aspect of the present invention, there is provided an anti-rhodopsin monoclonal antibody having different affinities to rhodopsin and metarhodopsin and a hybridoma capable of producing the monoclonal antibody.

In a fourth aspect of the present invention, there is provided a method for photochemical detection of a rhodopsin thin layer which comprises reacting the anti-rhodopsin monoclonal antibody with the rhodopsin thin layer previously exposed to light and detecting the photochemical reaction of the rhodopsin.

In a fifth aspect of the present invention, there is provided a hybrid antibody which can concurrently recognize rhodopsin and the thin layer constituent molecule, and a hybrid hybridoma capable of producing the hybrid antibody.

In a sixth aspect of the present invention, there is provided a process for preparing a rhodopsin thin layer which comprises immobilizing rhodopsin on a thin layer comprising the thin layer constituent molecule which is recognized by the hybrid antibody and a rhodopsin thin layer obtained by the process.

BRIEF DESCRIPTION OF THE DRAWINGS

FIGS. 1A–H are graphs showing antibody productivity of B6, C1, C6, C11, C15, D9, D11 and D24 cell lines respectively, in serum-free culture.

FIGS. 2A and B are graphs showing the results of tapping culture of D11 strain. FIG. 2A plots IgG concentration versus culture time. FIG. 2B plots cell concentration versus culture time.

FIGS. 5A and 5B diagrammatically illustrate how rhodopsin can be arranged and immobilized on phospholipid membrane by the hybrid antibody according to the present invention.

FIG. 6A diagrammatically illustrates that rhodopsin is not immobilized by anti-DNP monoclonal antibodies bound to a DNP-phospholipid membrane.

DETAILED DESCRIPTION OF THE INVENTION

Figure 3:
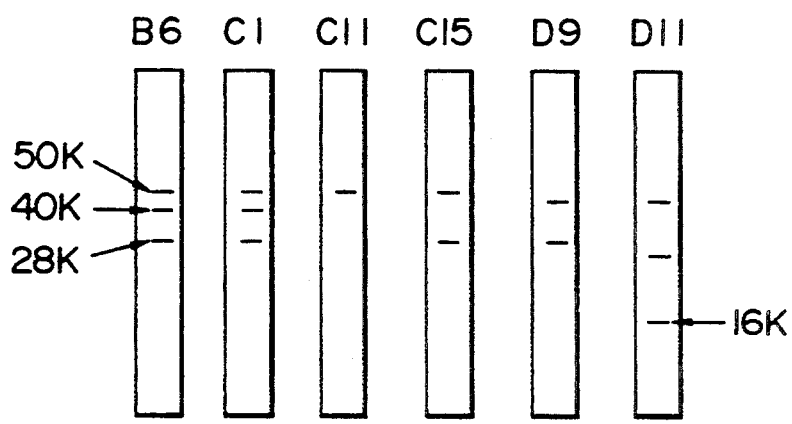
FIG. 3 indicates the results of immunoblotting of antibodies produced by B6, C1, C6, C11, C15, D9, D11 and D24 strains.

Hereinafter the present invention is described in detail.

The anti-rhodopsin monoclonal antibody can be produced by culturing a hybridoma constructed by so-called cell fusion. The anti-rhodopsin monoclonal antibody-producing hybridoma can be established by constructing hybridomas from antibody-producing cells and myeloma cells and cloning a hybridoma capable of producing the anti-rhodopsin antibody. The anti-rhodopsin monoclonal antibody-producing hybridoma is proliferated in mouse abdomen or in an cell culture equipment to obtain the antibody.

As the antibody-producing cells, there are used mouse spleen cells which are prepared by an animal immunized using as an antigen rhodopsin or metarhodopsin or a mixture of rhodopsin and metarhodopsin. As the immunizing antigen, crude or purified standard antigen may be used. The crude standard antigen is a protein extract obtained by extracting microvilar membrane of eyeball retina with a nonionic surfactant such as digitonin, octyl glucoside, heptyl glucoside, sugar ester, or the like which is used as a membrane protein extracting agent. The purified standard antigen can be obtained by applying the protein extract to ion exchange chromatography and affinity chromatography. Rhodopsin, metarhodopsin or a mixture of rhodopsin and metarhodopsin can be prepared by a method suitable for species of animal source. In the case of, for example, octopus rhodopsin, the mixture of rhodopsin and metarhodopsin can be prepared by exposing a solution of the crude or purified standard antigen to a blue light. Where the crude or purified standard antigen solution is exposed to a red light of 580 nm or longer, rhodopsin can be prepared. Metarhodopsin can be prepared by exposing a solution of the crude or purified standard antigen having pH of at least 10 to an orange light and then reducing its pH to 7 or below. These antigens are mixed with adjuvant and the mixture is injected to mouse under a safe red light to immunize the animal. The immunization is effected by injecting the antigen in a single dose of 40 to 100 $\mu$g, when calculated as protein weight, subcutaneously, intravenously or intraperitoneally, 2 to 4 times very 2 to 3 other weeks. Since some of the membrane protein extracting agents such as digitonin or sugar ester are toxic, it is necessary to test them in advance and determine a dose allowable to the body. Also where an extracting agent strongly toxic to mouse is contained in the antigen, in vitro immunization may be adopted.

The cell fusion may be performed in a manner similar to the method of Kohler and Milstein. As a partner to be fused, there may be utilized myeloma cells such as BALB/c mouse-derived X63 cells, P3U1 cells, NS-1 cells and SP2 cells, etc. B cells collected from the mouse spleen are mixed with the myeloma cells in 2 to 10 times. After centrifugation, the supernatant was completely removed by suction to give a pellet mixture of the myeloma cells and B cells. After the pellets are thoroughly loosened, 30 to 50% polyethylene glycol (molecular weight, 1000 to 4000) previously heated to 37° C. is added to the pellets followed by reacting at 30° to 37° C. Then, serum-free medium is dropped to and mixed with the system to terminate the reaction. After serum-free medium is further added in large quantities, the cells are recovered by centrifugation. The cells are suspended in HAT medium (containing hypoxanthine, aminoputerine and thymidine). The suspension is dispensed in a 96-well plate followed by incubation at 37° C. The half of the medium is removed by suction every 2 other days on 3 or 4 days after the incubation and instead, fresh HAT medium is supplemented to proliferate hybridoma alone. After the hybridoma is sufficiently proliferated, a hybridoma capable of producing a desired anti-octopus rhodopsin antibody is selected by enzyme linked immunosorbent assay (hereafter abbreviated as ELISA). The selected hybridoma is cloned by limiting dilution to give an anti-octopus rhodopsin antibody-producing clone.

The clone is transplanted to the abdomen of BALB/c mouse previously administered with pristane and 10 to 14 days after, the ascites is collected to give the antibody. The antibody may also be produced by culturing the clone in an animal cell culture equipment., The antibody is purified from the ascites or the medium via steps including fractionation with ammonium sulfate, ion exchange chromatography, etc.

To obtain the anti-rhodopsin monoclonal antibody of the present invention capable of recognizing a stable site of the rhodopsin molecule without inhibiting the photochemical reaction of rhodopsin, the desired antibody may be selected as follows in the case of octopus rhodopsin.

The purified octopus rhodopsin described above is mixed with the resulting antibody in the presence of a nonionic surfactant such as digitonin, sugar esters, etc. followed by incubation at 37° C. for 1 to 4 hours. By reacting octopus rhodopsin with the antibody in the presence of a nonionic surfactant and then performing ultrafiltration in the presence of the surfactant, the antibody-bound octopus rhodopsin can be isolated from the unbound octopus rhodopsin. A concentration of the surfactant may be 2% or less, preferably 0.05 to 0.2%. After incubation, the unreacted octopus rhodopsin is isolated through ultrafiltration membrane which does not permit to pass molecules having a molecular weight of 100,000 or more. The ultrafiltration membrane is not limited to such a membrane that does not permit to pass molecules having a molecular weight of 100,000 or more, but any membrane is usable so long as octopus rhodopsin and the antibody are fractionated from each other through the membrane. After the buffer is added to the fractionated solution containing molecules having a molecular weight of 100,000 or more, phosphate buffered saline (PBS) containing the surfactant may be supplemented to the mixture to make the volume the original one. Ultrafiltration followed again. To isolate the antibody-bound octopus rhodopsin and the unbound tacorhodopsin from each other, carrier-free electrophoresis, etc. may be applied, in addition to ultrafiltration, and any other techniques may be used as far as they do not injure the bond between the antibody and octopus rhodopsin. Immediately after ultrafiltration, the fractionated solution is exposed to a red light of 560 nm or longer and a blue light of 350 nm to 460 nm for about 10 to about 60 seconds. The all spectra are measured between 200 nm and 650 nm, using a spectrophotometer. The maximum absorption when the red/blue lights are alternately irradiated is determined; by selecting the antibody showing alternately changing the absorption maximum at about 475 nm by exposure to the red light and the absorption maximum at about 500 nm by exposure to the blue light, antibodies which do not inhibit the photoreaction of octopus rhodopsin can be selected.

The C-terminus of octopus rhodopsin, whose molecular weight is about 10,000, is more acceptable to protease digestion. The antibody recognizing the site of the C-terminus is not suitable for immobilizing octopus rhodopsin. So, the selected antibodies are examined as to an ability of recognizing limited tryptic fragments. Purified octopus rhodopsin is mixed with trypsin in a ratio of 50 to 200:1 followed by incubation at 37° C. for 5 to 40 minutes. The mixing ratio of trypsin is not particularly limited but the optimum conditions are chosen in every run. The reaction solution is mixed with SDS-treated solution containing mercaptoethanol and the resulting mixture is heated at 100° C. for 1 to 5 minutes. After electrophoresis on SDS-polyacrylamide gel, the system is transferred onto a nitrocellulose membrane. The selected antibodies are acted in accordance with ELISA to be examined the ability of recognizing the tryptic fragments. From these antibodies, antibodies which can recognize the digestion product having a molecular weight of about 16,000 or about 28,000 but can not recognize the C-terminus site having a molecular weight of about 10,000 are selected.

By the foregoing steps, the antibodies which do not inhibit the photochemical reaction but are capable of recognizing a stable site of the rhodopsin molecule can be constructed as anti-rhodopsin monoclonal antibodies for immobilizing rhodopsin.

Using the anti-rhodopsin monoclonal antibody of the present invention which can recognize the stable site of the rhodopsin molecule without inhibiting the photochemical reaction of rhodopsin, rhodopsin can be immobilized onto a carrier. That is, rhodopsin can be immobilized onto, for example, an activated microsphere by covalently binding the anti-rhodopsin monoclonal antibody to the microsphere via bismaleimide group, etc., then suspending the antibody-bound microsphere in a rhodopsin solution and then performing incubation. Therefore, elements such as photosensors, optical memory, etc. using rhodopsin can be provided by utilizing the anti-rhodopsin monoclonal antibody of the present invention.

In order to obtain the anti-rhodopsin monoclonal antibody of the present invention having different affinities to rhodopsin and metarhodopsin, the desired antibody may be selected as follows.

That is, the anti-rhodopsin monoclonal antibody of the present invention having different affinities to rhodopsin and metarhodopsin can be constructed by competitively reacting both rhodopsin and metarhodopsin antigens with the antibodies produced from hybridomas, detecting the presence or absence of the affinities by ELISA and selecting the antibody having different affinities.

Using the anti-rhodopsin monoclonal antibody of the present invention having different affinities to rhodopsin and metarhodopsin, the photochemical reaction can be detected.

That is, the photochemical reaction of rhodopsin in a thin layer can be detected using the anti-rhodopsin monoclonal antibody in combination with a method for detecting antigen-antibody reaction. For example, in octopus rhodopsin, its photochemical reaction can be detected as follows. After exposure of the rhodopsin thin layer to a red light or a blue light, antigen-antibody-reaction is carried out using the anti-rhodopsin monoclonal antibody having different affinities to rhodopsin and metarhodopsin. Then, an amount of the antibody bound to the thin layer is determined by ELISA, the fluorescent antibdoy method or the like. By comparing the amount of the antibody bound to the rhodpsin thin layer previously exposed to the red light or blue light, namely, by assaying a difference in the binding amounts, the photochemical reaction of the rhodopsin thin layer can be detected.

Therefore, it becomes possible to assay the photochemical reaction of rhodopsin on a thin layer, by antigen-antibody reaction of the rhodopsin in a thin layer, which has been exposed to lights having different wavelength, and the anti-rhodopsin monoclonal antibody having different affinities to rhodopsin and metarhodopsin, in combination with a method in which the antigen-antibody reaction can be amplified.

The hybrid antibody of the present invention which can concurrently recognize rhodopsin and the thin layer components can be obtained by fusing the hybridoma capable of producing the anti-rhodopsin antibody obtained as described above with a hybridoma capable of producing anti-thin layer constituent molecule antibody thereby to construct the fused cell having antibody genes of the two cells, namely, hybrid hybridoma.

The hybridoma capable of producing anti-thin layer constituent molecule antibody can be prepared by fusing mouse spleen cells from an animal immunized with the thin layer constituent molecule as antigen with myeloma cells, as described above.

As the thin layer constituent molecule, any molecule may be used so far as it has immunogenicity and is capable of producing an antibody to the thin layer constituent molecule. In the case that immunogenicity is lacking as in phospholipids, hapten is bound to phospholipids to construct anti-hapten antibody. In the present invention, dinitrophenyl (DNP), trinitrophenyl (TNP), p-azobenzoate, etc. may be used as hapten but in view of high stability, it is advantageous to use DNP. On the other hand, any organic thin layer which is a substrate for arranging and immobilizing rhodopsin may be used so long as hapten is bound to the thin layer. However, it is particularly preferred to use phospholipid since it is easy to form a monolayer film. For preparing phospholipid, dipalmitoyl phosphatidyl choline (DPPC), dimyristoyl phosphatidyl choline (DMPC), etc. may be used. In particular, the film prepared using DPPC is suited for the purpose of the present invention, since it has a regular structure and forms a stable film over a wide area. In order for antigen to stimulate lymphocyte to produce antibodies in the preparation of antibodies to DNP, a molecular weight of about 10,000 or more is necessary. Accordingly, BSA-DNP obtained by binding DNP to BSA (protein having a molecular weight of 69,000) is used as the antigen. With this antigen, antibodies not only to DNP or BSA but also to the sites containing parts of DNP and BSA might be produced. It is thus necessary to select antibodies binding only to DNP.

The fused cell of hybridoma capable of producing the anti-rhodopsin antibody with hybridoma capable of producing the anti-thin layer constituent molecule antibody, namely, hybrid hybridoma can be selected using HAT medium.

For the HAT selection, it is necessary to prepare enzyme-deficient cells from the respective hybridomas. When hybridoma is treated with a certain chemical to render the hybridoma resistant to the chemical, the hybridoma lacks HGPRT (hypoxanthine quantine phosphoribosyl transferase) or TK (thymidine kinase). If one is lacking a HGPRT and another is lacking of TK, only hybrid hybridoma constructed by fusion of different cells can acquire two enzymes and grow in HAT medium, whereby HAT selection can be made. All of the cells obtained by the HAT selection do not acquire antibody genes of the respective hybridomas. Thus, these cells are subjected to primary selection by ELISA, cloning and then further secondary selection by ELISA, whereby the desired hybrid hybridoma can be obtained. Since this hybrid hybridoma acquires the antibody genes from two hybridomas, antibodies are produced in 10 combinations. In order to obtain the hybrid antibody capable of recognizing rhodopsin and the thin layer constituent molecule, it is necessary to isolate and purify the hybrid antibody from these antibodies, using affinity chromatography, etc.

The hybrid antibody may also produced chemically. The S—S bond present in the hinge region of the antibody can be cleaved with a reducing agent. Therefore, the anti-rhodopsin antibody and the anti-thin layer constituent molecule antibody are treated with a reducing agent such as dithiothreitol (DTT) or mercaptoethanol, respectively. Then, the halves of the respective antibodies are combined to obtain the hybrid antibody capable of concurrently recognizing rhodopsin and the thin layer constituent molecule. For preparing the hybrid antibody, either such a chemical method or the aforesaid biological method may be used.

Using the hybrid antibody of the present invention which can concurrently recognize rhodopsin and the thin layer constituent molecule, rhodopsin can be immobilized on the thin layer. The hybrid antibody may be arranged and immobilized on the thin layer as it is. Alternatively, the Fc part of the hybrid antibody may be cut off by treating with pepsin and the remaining $F(ab')_2$ alone is used for the arrangement and immobilization.

In the present invention, rhodopsin can be regularly arranged and immobilized on the thin layer to the same extent as the arrangement of the thin layer constituent, by using the hybrid antibody capable of concurrently recognizing rhodopsin and the thin layer constituent molecule. It is thus possible to develop a precise photosensor or a super high density photomemory, etc.

Hereafter, the present invention is concretely described with reference to the examples but is not deemed to be limited to these examples.

EXAMPLE 1

1) Purification of Antigen

Rhodopsin is a membrane protein present in rods of visual cells which construct the retina.

Firstly, the rods were fractionated. The following procedures were carried out in a dark room.

After the retinas withdrawn and recovered from 100 eyeballs of *Paroctopus defleini* were suspended in 1.2 liter of A-buffer [10 mMMOPS-NaOH, pH 7.4, 20 μM p-amino-phenylmetasulfonyl fluoride hydrochloride (PAPASF)], large solids were removed through a gauze. Then, the suspension was centrifuged at 40,000×g at 4° C. for 30 minutes to recover outer segment of visual cells constituting the retinas. The outer segment was suspended in 300 ml of 34% sucrose-containing A-buffer and the sucrose suspension was centrifuged under conditions of 40,000×g for an hour. The supernatant was recovered to give microvilar membrans. After A-buffer was added to the supernatant to make the volume 600 ml, centrifugation was performed under conditions of 40,000×g at 4° C. for 20 minutes to give microvilar membrane pellets. Then, the pellets were resuspended in A-buffer and the suspension was centrifuged under the same conditions. This procedure was repeated 3 times to effect rinsing. The microvilar membrans were suspended in digitonin solution (2% digitonin, 100 mM $Na_2HPO_4$-$KH_2HPO_4$, pH 6.8). The suspension was shaken for an hour to extract rhodopsin. Next, the residue was removed by centrifugation (25,000×g, 1 hour) to give the extract. Again the residue was extracted with digitonin to recover the rhodopsin.

In order to remove omochrome from the digitonin extract, ion exchange chromatography was performed on DEAE-Sephacel (manufactured by Pharmacia). A column was packed with 5 ml of DEAE-Sephacel and equilibrated with B-buffer (0.1% digitonin, 50 mM Na$_2$HPO$_4$-KH$_2$HpO$_4$, pH 6.8). Thereafter, the extract was charged and the B-buffer was passed through the column to obtained a fraction having absorptions at 280 nm and 480 nm. Then, rhodopsin was isolated by affinity chromatography using Con A-Sepharose (manufactured by Pharmacia). A column was packed with 10 ml of Con A-Sepharose and equillbrated with C-buffer (0.2% digitonin, 50 mM Tris-HCl, pH 7.0). Thereafter, the fraction was charged and the C-buffer was passed through the column several times. Then, rhodopsin was eluted with a buffer containing 1M α-methylglucoside.

2) Immunization of Mouse

After the digitonin concentration was previously adjusted to 0.1% or less with CENTRICON 30K (manufactured by Amicon Co., Ltd.), the purified octopus rhodopsin was diluted with PBS to prepare octopus rhodopsin solution having a protein concentration of 200 μg/ml. The octopus rhodopsin solution was diluted and the dilution was intraperitoneally injected to BALB/c female mouse by the following method to sensitize with octopus rhodopsin.

TABLE 1

| Number of Time | Method for Sensitization | | |
|---|---|---|---|
| | Amount of Protein | Amount of Adjuvant | Dose Injected |
| First immunization | 100 μg | 15 μg | 0.5 ml |
| Second - third immunization | 20 μg | 15 μg | 0.5 ml |
| Final immunization | 40 μg | 30 μg | 0.5 ml |

Intervals:

First immunization [—2 weeks—] Second immunization [—2 weeks—] Third immunization [—2 weeks—] Final immunization Adjuvant:

N-acetylmuramyl-L-alanyl-D-isoglutamine (made by Sigma Co. , Ltd. )

3) Cell Fusion

Three days after the final immunization, spleen was withdrawn from the mouse and provided for cell fusion. After the spleen was loosened in 1:1 medium mixture of HAM medium (manufactured by Nisshui Pharmaceutical Co., Ltd.) and IMDM medium (manufactured by Sigma Co., Ltd.) (hereinafter referred to as HI medium), centrifugation (1600 rpm, 5 minutes) was carried out to recover spleen cells. The cell pellets were resuspended in HI medium. The spleen cells suspension and myeloma cells (P3U1 strain), which were obtained by culturing in HI medium containing 10% calf fetal serum and collecting by centrifugation (1000 rpm, 5 minutes), were resupended in serum-free HI medium followed by centrifugation. The procedure was repeated twice to prepare serum componentfree myeloma cell suspension.

The two cell suspensions were mixed to have spleen cells of $2 \times 10^8$ and myeloma cells of $4 \times 10^7$. The mixture was centrifuged (1800 rpm, 5 minutes) to give pellet mixture. After the supernatant was completely removed, the pellets were mixed. To the mixture was dropped 1 ml of 50% polyethylene glycol 1500 (manufactured by Boehringer Mannheim Co., Ltd.) previously heated to 37° C. over one minute. After stirring for a minute, 1 ml of HI medium was dropped over a minute. After 8 ml of HI medium was further dropped over 3 minutes, the cells were recovered by centrifugation (1000 rpm, 5 minutes).

The cell pellets were suspended in 40 ml of HAT medium [HI medium supplemented with HAT solution (manufactured by Flow Laboratories)] containing 20% calf fetal serum. The suspension was separately charged in each well of a 96 well microplate (manufactured by Corng Co., Ltd.). Four days after, 100 μl of the HAT medium was supplemented and after that, fresh HAT medium was exchanged by 50% every 2 other days. Ten days after, 50% of the medium was exchanged every 2 other days with HT medium [HI medium supplemented with HT solution (manufactured by Flow Laboratories)] containing 20% calf fetal serum.

4) Selection of Hybridoma

With respect to the wells of colonies with large hybridoma, the supernatant was taken for sampling and a hybridoma capableof prodducing anti-octopus rhodopsin antibody was selected by ELISA.

After 50 82 1 of purified octopus orhodopsin (0.01 mg/ml) was separately charged in each well of a microtiter plate previously coated with poly-L-lysine, the system was settled at 4° C. for about 18 hours. One minute after separately charging 50 μl of 1% glutaraldehyde, rinsing was performed 3 times with 200 μl of phosphate buffered saline (PBS). Furthermore, 200 μl of blocking solution [BLOCK ACE (manufactured by Dainippon Pharmaceutical Co., Ltd.) diluted with PBS to one-fourth] was added and the resulting mixture was settled at 37° C. for an hour to block the non-adsorbed portion in each well. After rinsing 3 times with PBS, 100 μl of the supernatant was added and the mixture was settled at 37° C. for an hour. After rinsing 3 times with PBS containing 0.1% Tween 20, 100 μl of biotinated anti-mouse IgG antibody (ABC Kit manufactured by Bector-Stein Co., Ltd.) solution was added and the mixture was settled at 37° C. for an hour. After rinsing 3 times with PBS, 100 μl of biotinated peroxidase and avidin solution mixture was added and the mixture was settled at 37° C. for 30 minutes. After rinsing 3 times with PBS, 0.1M citrate buffer (pH 5.4) of orthophenylenediamine containing 0.001% hydrogen peroxide was added and absorbance was measured at a wavelength of 412 nm. At the same time, ELISA was performed with 0.1% digitonin solution.

As the result, 35 samples recognized octopus rhodopsin, and among them, 6 samples recognized digitonin.

With respect to the hybridomas which recognized octopus rhodopsin alone, hybridoma cell lines B6, C1, C6, C11, C15, D9, D11 and D24 were obtained by the limiting dilution method.

5) Preparation of Monoclonal Antibody

In order to make purification of the antibody easy, the hybridomas were subcultured in serum-free medium (E-RDF medium: manufactured by Kyokuto Pharmaceutical Co., Ltd.) every 3 other days. Strains having stable antibody productivity were thus selected by serum-free incubation.

Any of the strains proliferated in the serumfree medium. As illustrated in FIG. 1, however, after Subcultures 24 times, the antibody productivity of B6, C1, C11, C15, D9 and D11 strains did not change as compared to the initial stage of subculture, but C6 and D24 strains showed reduction in the antibody productivity. Based on the results, B6, C1, C11, C15, D9 and D11 strains were selected as candidates for preparing monoclonal antibodies.

Regarding each strain, suspension culture was performed using a tapping culture flask (manufactured by Ikemoto Rika Co., Ltd.).

A volume of the flask was 200 ml and a volume charged was 70 ml. A temperature and shake number of a tapping stirrer were set at 37° C. and 350 rpm, respectively. The gaseous phase of the flask was replaced by 5% $CO_2$ air. A fresh medium was exchanged for the medium every other day.

As an example of incubation, the process of culturing D11 strain is illustrated in FIG. 2.

After each culture solution was concentrated to approximately 1/5 through ultrafiltration membrane (cut-off molecular weight: 200,000; manufactured by Toyo Advantech Co., Ltd.), salting out with ammonium sulfate and dialylsis against PBS were performed to give crude antibody solution. The crude solution was then purified using a monoclonal antibody purification system (manufactured by Bio-Rad Co., Ltd.).

6) Property of Monoclonal Antibody (1) Class and subclass

Class and subclass of each monoclonal antibody were assayed using mouse monoclonal antibody isotyping kit (manufactured by Amersham Co., Ltd.).

As the result, the class of B6, C1, C15 and D11 strains-producing antibodies was IgG and the subclass was IgG2a for B6-producing antibodies and IgG1 for the other antibodies. The class of C11 and D9-producing antibodies was IgM.

(2) Influence of antibodies on the photochemical reaction of octopus rhodopsin

After the antibodies described above were bound to purified octopus rhodopsin, red/blue lights were alternately irradiated to examine change in the absorption maximum.

After purified octopus rhodopsin and the antibodies (B6, C1, C15, C11, D9 and D11-producing antibodies) were mixed in a molar ratio of 3:2, respectively, using 0.1% digitonin-containing PBS, incubation was carried out at 37° C. for 2 hours. Then, the unreacted rhodopsin was removed through ultrafiltration membrane (cut-off molecular weight: 200,000; manufactured by Toyo Advantech Co., Ltd.). Immediately, the supernatant was reverted to the original volume with 0.1% digitonin-containing PBS. The supernatant was out at a distance of 1 cm from red/blue lights filter (glass filter 0–58, V-44, manufactured by Toshiba) mounted on a slide objector in a dark room and exposed to the lights for 10 seconds. The all spectra were measured by a spectrophotometer (manufactured by Hitachi Ltd.) to examine the absorption maximum values after exposure to the red/blue lights.

Table 2 shows changes in the absorption maximum values after exposure to the red/blue lights. For control, the system of octopus rhodopsin (OR) alone and the system of mixing with bovine serum albumin (BSA) were examined.

TABLE 2

| | Influence of Antibody of Photochemical Reaction of octopus rhodopsin | |
|---|---|---|
| | Absorption Maximum (nm) | |
| Sample | Exposure to Red Light | Exposure to Blue Light |
| OR | 475 | 506 |
| OR + BSA | 476 | 502 |
| OR + B6-producing antibody | 475 | 500 |
| OR + C1-producing antibody | 477 | 502 |
| OR + C11-producing antibody | 474 | 503 |
| OR + C15-producing antibody | 477 | 503 |
| OR + D9-producing antibody | 474 | 501 |
| OR + D11-producing antibody | 474 | 501 |

In any of the antibodies, the absorption maximum values shifted alternately after exposure to red/blue lights, as in the case of octopus rhodopsin alone. It is thus noted that these antibodies do not inhibit the photochemical reaction of octopus rhodopsin.

(3) Ability of octopus rhodopsin for recognizing limited tryptic fragments

When purified octopus rhodopsin is specifically digested or cleaved with trypsin, the digestion or clearvage product having a molecular weight of about 40,000, in which the C-terminal region of about 10,000 molecular weight has been withdrawn from octopus rhodopsin (molecular weight, about 50,000) and further the digestion products having molecular weights of about 16,000 and 28,000 are formed. The ability of each antibody for recognizing these specific digestion products was examined by immunoblotting technique.

Purified octopus rhodopsin was mixed with tyrpsin (manufactured by Worthington Biochemical Co., Ltd.) in 100:1 followed by incubation at 37° C. for 30 minutes. Immediately after the incubation, the system was mixed with an SDS treating solution and the mixture was heated at 100° C. for 5 minutes. The SDS-treated system was subjected to electrophoresis on SDS-phast Gel (manufactured by Pharmacia) using PHAST SYSTEM ELECTROPHORESIS EQUIPMENT (manufactured by Pharmacia). Then, a wet nitrocellulose membrane was put on the gel and heated at 70° C. for 20 minutes from the bottom of the gel to transfer rhodopsin and its tryptic fragments. The nitrocellulose membrane was blocked with a blocking agent (manufactured by Dainippon Pharmaceutical Co., Ltd.). After rinsing with PBS containing 0.1% Tween-20, the antibody was acted thereon. Subsequently, the procedure was performed by ELISA and finally, the nitrocellulose membrane was developed with 4-chloronaphthol.

The results of immunoblotting are illustrated in FIG. 3. The antibodies to B6, and C1 strains recognized the tryptic fragment having a molecular weight of about 40,000 but the antibodies to C11, C15, D9 and D11 strains did not recognize the tryptic fragment. The antibodies to B6, C1, C15, D9 and D11 strains recognized the digestion product having a molecular weight of about 28,000. The antibody to D11 strain recognized the digestion product having a molecular weight of 16,000.

From the results, it is noted that the antibodies to C15, D9 and D11 strains recognized the tryptic fragment having a molecular weight of about 40,000 as in the antibodies to B6 and C1 strains, since the tryptic fragments having molecular weights of about 16,000 and about 28,000 were the tryptic fragments from that having a molecular weight of about 40,000.

By the foregoing steps, the antibodies capable of recognizing the stable site of the structure without inhibiting its photochemical reaction could be constructed as the monoclonal antibodies for immobilizing octopus rhodopsin.

EXAMPLE 2

The antibody obtained in Example 1 was covalently bound to a carrier and octopus rhodopsin was then immobilized on the carrier and exposed to red/blue lights to examine the presence or absence of photochemical reaction.

After the D11-producing antibody was covalently bound to 30 mg of activated microsphere (diameter of about 3 μm; manufactured by Funakoshi Chemical Co., Ltd.], the carrier was recovered by centrifugation (3000 rpm, 10 minutes). The carrier was suspended in PBS and the suspension was centrifuged. This procedure was repeated twice followed by rinsing. The antibody-bound carrier was suspended in 0.1% digitonin-containing octopus rhodopsin solution (1.1 mg/ml). While gently stirring, the suspension was incubated, namely, reacted at 37° C. for 2 hours. After the carrier was collected by centrifugation, the carrier was suspended in 0.1% digitonin-containing PBS and the suspension was centrifuged for rinsing. The rinsed carrier was colored to a light orange color, showing that rhodopsin was immobilized thereon. The carrier was suspended in 0.1% digitonin-containing PBS and the suspension was dropped onto a quartz glass plate. After irradiating with red/blue lights through an optical fiber for 20 seconds in a dark room, change in absorption was determined with Spectro Multichannel Photodetector (manufactured by OTSUKA ELECTRONICS Co., Ltd.).

As the result, where the red light was irradiated, the absorption maximum was noted at 475 nm; where the blue light was irradiated, the absorption maximum was noted at 502 nm. By irradiating with red/blue lights alternately, the both absorption maxima were alternately shifted. In the case that the antibody-bound carrier alone was exposed to the red/blue lights similarly, such a change in the absorption maximum values was not observed. Therefore, the above change is attributed to the photochemical reaction of octopus rhodopsin immobilized by the antibody.

EXAMPLE 3

The anti-rhodopsin monoclonal antibody of the present invention having different affinities to rhodopsin and metarhodopsin was selected as follows.

(1) Difference in affinities to rhodopsin and metarhodopsin

The antibody obtained in Example 1 was competitively reacted with rhodopsin and metarhodopsin to examine its affinity.

After 50 μl of rhodopsin solution (containing 0.1% digitonin) was separately charged in each well of a 96 well immunoplate previously coated with poly-L-lysine, the system was settled at 37° C. for an hour. One minute after 50 μl of 1% glutaraldehyde solution was added to the mixture, rinsing was performed 3 times with PBS. Furthermore, 200 μl of blocking solution [BLOCK ACE (manufactured by Dainippon Pharmaceutical Co., Ltd.) diluted with PBS to one-fourth] was added and the mixture was settled at 37° C. for an hour to block the non-adsorbed portion in each well. After rinsing 3 times with PBS, 25 μl of each antibody solution and 25 μl of rhodopsin solution or metarhodopsin solution appropriately diluted were added and the mixture was settled at 37° C. for an hour. After rinsing 3 times with PBS containing 0.1% Tween 20, 100 μl of biotinated anti-mouse IgG antibody (ABC Kit manufactured by Bector-Stein Co., Ltd.) solution was added and the mixture was settled at 37° C. for an hour. After rinsing 3 times with PBS, 100 μl of biotinated peroxidase and avidin solution mixture was added and the mixture was settled at 37° C. for 30 minutes. After rinsing 3 times with PBS, 0.1M citrate buffer (pH 5.4) of orthophenylene-diamine containing 0.001% hydrogen peroxide was added and absorbance was measured at a wavelength of 412 nm.

Figure 4:
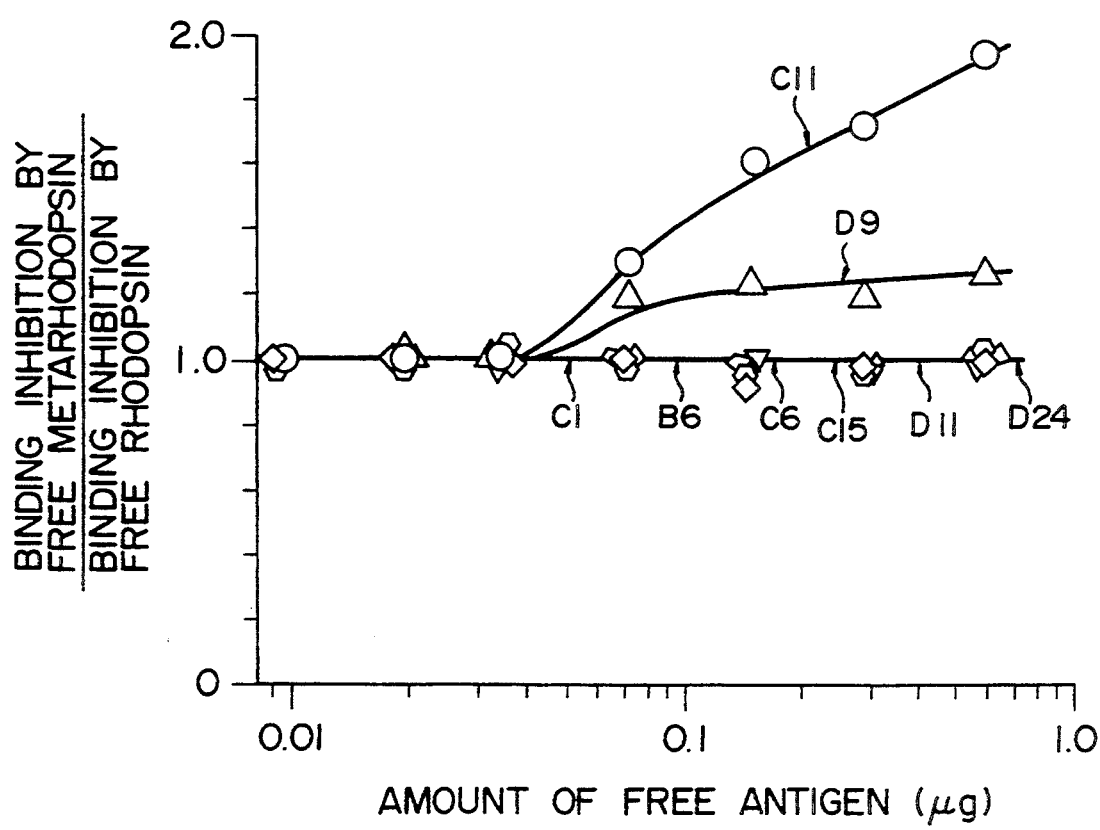
FIG. 4 is a graph showing the presence or absence of affinity of anti-octopus rhodopsin antibody to rhodpsin and metarhodopsin.

The results are illustrated in FIG. 4, wherein the ordinate designates the ratio of the binding inhibition by free rhodopsin and metarhodopsin, and the abscissa designates an amount of the free antigen. The C1, B6, C6, C15, D11 and D24 antibodies showed no difference, irrespective of rhodopsin and metarhodopsin used as the free antigen, whereas the C11 and D9 antibodies were inhibited by the free antigen, metarhodopsin. That is, it has been made clear that the two antibodies had high affinity to metarhodopsin.

(2) Recognition site

Regarding the 2 antibodies described above, their recognition sites were examined.

Now, the primary structure of octopus rhodopsin has been clarified by Y. A. Ovchinnikov et al. and the secondary structure that 7 helices piece through the membrane is assumed [FEBS Letters, Vol. 232, No. 1, 69–72 (1988)]. The fragment having a molecular weight of 28,000 which was recognized by C11 and D9 antibodies is a region containing the first to fifth helices of the N-terminus. Accordingly, a peptide whose amino acid sequence was that of a part of the cytoplasmic site in this region was synthesized and bound to bovine serum albumin (BSA) via carbodiimide, where the presence or absence of crossreactivity with the antibodies were studied by ELISA. Synthesis of the peptide was performed by the Fmoc method using a peptide synthesizer (manufactured by Pharmacia).

The measurement results showing the crossreactivity with the bovine serum albumin (BSA)-bound peptide are shown in Table 3. In this case, the amino acid sequence of the peptide is as described below. The results obtained with other antibodies are also shown in Table 3.

TABLE 3

| Monoclonal Antibody | Absorbance $A_{412}$ | | |
|---|---|---|---|
| | Octopus rhodopsin | Antigen Peptide-BSA | BSA |
| C1 | 0.40 | 0.10 | 0.04 |
| B6 | 0.64 | 0.09 | 0.07 |
| C6 | 0.60 | 0.08 | 0.08 |
| C11 | 0.28 | 0.25 | 0.08 |
| C15 | 0.53 | 0.03 | 0.06 |
| D9 | 0.49 | 0.18 | 0.06 |
| D11 | 0.49 | 0.03 | 0.02 |
| D24 | 0.22 | 0.19 | 0.21 |

The results reveal that the C11 and D9 antibodies were cross-reactive with the peptide. Since the peptide was in the hydrophilic region connecting the third helix to the fourth helix, it was also assumed that the both antibodies would recognize the region. (Amino acid sequence of the synthetic peptide)

N-terminal Val-Ile-Gly-Arg-Pro-Met-Ala-Ala-Ser-Lys-Lys-Met-Ser C-terminal

EXAMPLE 4

Using the C11 antibody, the presence or absence of the photochemical reaction in the Octopus rhodopsin thin layer was examined.

The octopus rhodopsin thin layer was constructed as follows. Pure water was charged in Langmuir Trough (manufactured by Joyce Level Co., Ltd.) and 100 μl of octopus rhodopsin solution containing 0.2% digitonin was spread over water followed by compression to 50 mN/m. As compared to digitonin, π-A curve of the octopus rhodopsin solution showed a larger increasing rate of the surface pressure, confirming that octopus rhodopsin molecule was packed at the gas-liquid interface. Therefore, a quartz substrate went up and down 4 times at a dipping speed of 5 mm/min to transfer the film on the liquid surface onto the substrate. The octopus rhodopsin thin film was exposed to the red or blue light under a safe red light and, the presence or absence of the photochemical reaction was checked by ELISA, respectively.

The analytical operation was performed under the safe red light. Firstly, the quartz substrate with the octopus rhodopsin thin film was dipped in a blocking solution and heated at 37° C. for an hour. Then, the substrate was rinsed with PBS and then dipped in a C11 antibody solution followed by incubating at 37° C. for an hour. Thereafter, the procedure was carried out in a manner similar to Example 1. Finally, the quartz substrate was dipped in orthophenylenediamine solution (pH 5.4) containing 0.001% hydrogen peroxide and absorbance of the solution was measured at a wavelength of 412 nm. For control, similar procedures were performed also with the D11 antibody and anti-dinitrophenyl antibody.

The results of assaying the photochemical reaction of octopus rhodopsin in this film are shown in Table 4. With the D11 antibody, there was no change in absorbance in the octopus rhodopsin thin film exposed to the red light and to the blue light. With the C11 antibody, however, its absorbance was higher than in the case of exposure to the blue light. It is thus made clear that there was a difference in absorbance between the octopus rhodopsin thin film exposed to the red light and to the blue light, resulting in change due to the photochemical reaction.

TABLE 4

| Sample | Absorbance $A_{412}$ | | |
|---|---|---|---|
| | C11 Antibody | C11 Antibody | Anti-Dinitro-Phenyl Antibody |
| Octopus rhodopsin thin film exposed to red light | 0.16 | 0.38 | 0.08 |
| Octopus rhodopsin thin film exposed to blue light | 0.32 | 0.39 | 0.07 |

As stated above, the photochemical reaction of Octopus rhodopsin in this layer could be detected by the antibody having different affinities to rhodopsin and metarhodopsin in combination with the method such as enzyme-linked immunoassay, etc. in which antigen-antibody reaction could be amplified.

EXAMPLE 5

[I] Preparation of anti-DNP antibody

Anti-DNP antibody was prepared in a manner similar to Example 1. In this case, DNP was bound to BSA and four mice were immunized with BSA-DNP, using the same as antigen. There is a possibility that this antigen would produce antibodies not only to DNP or BSA but also to the sites containing a part of DNP and BSA. It was thus deviced to select the antibodies binding only to DNP. That is, the reaction with poly-L-lysine (PLL)-DNP obtained by binding DNP to PLL was also assayed by ELISA, in addition to the reaction with BSA and BSA-DNP and antibodies binding only to DNP were selected. As the result, 13 out of 768 samples were assumed to produce antibodies binding only to DNP. Among them, optionally selected two antibodies were cloned to obtain 5 monoclonal hybridomas capable of stably producing the anti-DNAP antibody. Optionally selected one out of the five hybridomas was cultured and the antibody secreted in the medium was purified by means of ultrafiltration, salting out and dialysis.

It was examined if the thus obtained antibody could bind to DNP-bound phospholipid LB membrane (DNP-phospholipid LB membrane). On a quartz glass plate, the DNP-phospholipid LB membrane was constructed and the anti-DNP antibody was reacted to perform ELISA. In order to show that the reaction is through the bond by antigen-antibody reaction, anti-rhodopsin antibody was reacted for control, and ELISA was performed. Also in order to confirm that color formation is not caused by the reaction not associated with the antibody, ELISA was performed also with a sample to which no antibody was added. As the result, only the samples to which the anti-DNP antibody was added formed a color but the samples to which either the anti-rhodopsin antibody was added or no antibody was added did not form any color. That is, from the fact that the resulting anti-DNP antibody was bound to DNP-phospholipid LB membrane, it was revealed that the thus obtained antibody was no doubt the anti-DNP antibody.

[II] Construction of hybrid antibody

1) Preparation of chemical-resistant cell line

In order to prepare hybrid hybridoma by HAT selection, a hybridoma was firstly treated with a chemical to construct a chemical-resistant strain. As the anti-rhodopsin antibody-producing hybridoma, C1 strain obtained in Example 1 was used. C1 strain was treated with 8-azaguanine (8-AG) to make the strain C1 HGPRT-deficient. The anti-DNP antibody-producing hybridoma was treated with 5-bromodeoxyuridine (5-BDU) to render it TK-deficient strain. Firstly, treating concentrations were set stepwise to select the limiting concentration for inhibiting proliferation. At the same concentration, incubation was continued to come the chemical-resistant strain out.

a) Prepation of 8-AG-resistant hybridoma

The anti-rhodopsin antibody-producing hybridoma (C1) was cultured in medium containing 8-AG in 6 stepwise concentrations of 0.94 to 30 μg/ml. Four days after the effect of inhibiting proliferation was remarkable in a concentration of 30 μg/ml and hence, the incubation was further continued. Eighteen days after the cells which were considered to acquire chemical resistance were observed. When a part of the cells was cultured in HAT medium, the cells were dead and HGPRT deficiency was confirmed. Next, the cells were cloned to give 16 hybridomas having the anti-rhodopsin antibody productivity and having acquired 8-AG resistance.

b) Preparation of 5-BDU-resistant hybridoma

The anti-DNP antibody-producing hybridoma was cultured in medium containing 5-BDU in 6 stepwise concentrations of 3 to 60 μg/ml. Three days after 3, the effect of inhibiting proliferation was noted in each concentration, but the cells were dead in a concentration of 7.5 to 60 μg/ml. 5-BDU showed the effect of growth inhibition in a lower concentration than in 8-AG. Therefore, the cells in which proliferation was noted in concentrations of 3 and 6 μg/ml were stepwise adapted to a higher concentration in 1 to 2 days. As the result, the cells which could proliferate in a concentration of 60 μg/ml appeared 11 days after. By further continuing the incubation at this concentration, TK deficiency was confirmed in HAT medium and antibody productivity was assayed by ELISA to obtain 2 hybridomas.

2) Cell fusion

The anti-rhodopsin antibody-producing hybridoma (deficient of HGPRT) was fused with the anti-DNP antibody-producing hybridoma (deficient of TK) and HAT selection was performed to obtain hybrid hybridoma. The hybrid hybridoma was assayed by ELISA to select 126 cells capable of producing the antibody binding to both rhodopsin and DNP. Optionally selected 3 hybrid hybridomas were cloned and 27 strains were obtained as the cells having stable antibody productivity. From them, one strain having a high antibody productivity was selected to prepare hybrid antibody.

3) Preparation of hybrid antibody

The hybrid hybridoma was cultured and the antibodies secreted in the medium were purified by means of ultrafiltration, salting out and dialysis. From 10 kinds of antibodies contained in the above purified antibodies, the hybrid antibodies were purified by two step affinity chromatography. Firstly, purified sample was reacted with lysine-Sepharose 4B-DNP. After rinsing, eluate was obtained using 0.1N hydrochloric acid. As the result of ELISA, an amount of the anti-DNP antibody in the rinsing liquid was reduced as compared to that of the purified sample. It is thus assumed that the anti-DNP antibody would be bound to the carrier. Next, by performing affinity chromatography using rhodopsin as a carrier, the hybrid antibody can be collected. However, rhodopsin was required in large quantities for the affinity chromatography and hence, the following method was adopted. L-chain of the anti-rhodopsin antibody takes K type and the anti-DNP antibody takes λ type. By utilizing this difference, the hybrid antibody is bound to a carrier of anti-K chain antibody (agarose-avidin D-biotinated anti-K chain antibody) and elution was performed with 0.1N hydrochloric acid. By the procedure, the antibody mixture of the antibody capable of recognizing DNP but incapable of recognizing rhodopsin, and the hybrid antibody could be obtained. That is, the hybrid antibody could be obtained by the two step affinity chromatography technique described above.

[III] Preparation of rhodopsin thin layer

Using the hybrid antibody capable of concurrently recognizing rhodopsin and DNP, rhodopsin was immobilized as follows. The procedure is explained by referring to FIG. 5.

Figure 5C:
FIG. 5C is a photograph showing color formation following orthophenylenediamine treatment of peroxidase-labelled anti-rhodopsin monoclonal antibody bound to rhodopsin immobilized on a phospholipid membrane by an anti-DNP anti-rhodopsin hybrid antibody.
Figure 6B:
FIG. 6B is a photograph showing lack of color formation of the phospholipid membrane diagrammed in FIG. 6A following treatment with peroxidase-labelled anti-rhodopsin monoclonal antibody.

As is illustrated in FIG. 5(a), DNP-phospholipid membrane 2 was constructed on a quartz glass substrate 1 according to the LB method. After reacting hybrid antibody 3, rhodopsin 4 was added to react them. In order to confirm that the desired thin layer was formed, peroxidase-labeled anti-rhodopsin antibody 5 (D11) was reacted after rinsing, as illustrated in FIG. 5(b). After rinsing, orthophenylenediamine solution was added to check the presence or absence of color formation. As is illustrated in FIG. 5(b), rhodopsin was immobilized on the phospholipid membrane by the hybrid antibody so that the solution became yellow by the enzyme bound to the labeled antibody described above. It was thus confirmed that the intended purpose was achieved by this example. The results are shown in photographs of FIG. 5(c). FIG. 6 shows the results of comparative example for confirming the utility of the present invention. In the example illustrated in FIG. 6, anti-DNP antibody 6 was used instead of hybrid antibody 3 and the anti-DNP antibody was treated in a manner similar to FIG. 5. In this case, the anti-DNP antibody was bound to the DNP-phospholipid membrane and rhodopsin was not immobilized due to lack of the ability of recognizing rhodopsin, as shown in FIG. 6(a); therefore, the rhodopsin was flown out by rinsing so that the peroxidase-labeled anti-rhodopsin antibody was not bound thereto. As the result, no color was formed as shown in FIG. 6(b).

From the foregoing results, it was revealed that using the hybrid antibody capable of concurrently recognizing rhodopsin and DNP, rhodopsin could be arranged and immobilized on the phospholipid membrane and the rhodopsin thin layer having arrangement as regular as in the phospholipid membrane could be prepared.

What is claimed is:

1. An anti-rhodopsin monoclonal antibody which binds to octopus rhodopsin and octopus metarhodopsin, and which binds with a greater binding affinity to said octopus metarhodopsin than to said octopus rhodopsin, such that binding of said antibody to said octopus rhodopsin can be distinguished from binding of said antibody to said octopus metarhodopsin in an immunoassay, wherein said antibody binds to a site of said octopus rhodopsin or said octopus metarhodopsin without inhibiting light-induced rhodopsin-metarhodopsin interconversion of said octopus rhodopsin or said octopus metarhodopsin, and wherein said site is a polypeptide having the following amino acid sequence: Val-Ile-Gly-Arg-Pro-Met-Ala-Ala-Ser-Lys-Lys-Met-Ser.

* * * * *